(12) United States Patent
Shusta et al.

(10) Patent No.: US 8,293,495 B2
(45) Date of Patent: Oct. 23, 2012

(54) BLOOD-BRAIN BARRIER MODEL

(75) Inventors: Eric V. Shusta, Madison, WI (US); Christian Weidenfeller, Madison, WI (US); Clive Niels Svendsen, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 13/218,123

(22) Filed: Aug. 25, 2011

(65) Prior Publication Data

US 2011/0312018 A1 Dec. 22, 2011

Related U.S. Application Data

(62) Division of application No. 11/766,633, filed on Jun. 21, 2007.

(60) Provisional application No. 60/816,033, filed on Jun. 23, 2006.

(51) Int. Cl.
*C12Q 1/02* (2006.01)
*C12N 5/00* (2006.01)
*C12N 5/079* (2010.01)

(52) U.S. Cl. ........... 435/29; 435/373; 435/401; 435/325

(58) Field of Classification Search ........................ None
See application file for complete search history.

(56) References Cited

U.S. PATENT DOCUMENTS

| | | | | |
|---|---|---|---|---|
| 6,667,172 | B2 * | 12/2003 | Janigro et al. ............. | 435/297.4 |
| 2003/0103949 | A1 | 6/2003 | Carpenter et al. | |
| 2003/0203844 | A1 | 10/2003 | Delfani et al. | |

FOREIGN PATENT DOCUMENTS

WO   WO 03/040319   *   5/2003

OTHER PUBLICATIONS

Reubinoff et al, "Neural Progenitors from human embryonic stem cells", Nature Biotechnology, 2001, vol. 19, pp. 1134-1140.*
Schwartz et al, "Isolation and Characterization of neural Progenitor Cells from Post-Mortem Human Cortex", Journal of Neuroscience Research, 2003, vol. 74, pp. 838-851.*
Weidenfeller, et al., Differentiating embryonic neural progenitor cell induce blood-brain barrier properties, Journal of Neurochemistry, 2007, 101: 555-565.
Calabria, et al., Puromycin-purified rat brain microvascular endothelial cell cultures exhibit improved barrier properties in response to clucocorticoid induction, Journal of Neurochemistry, 2006, 97: 922-933.
Deli, et al., Permeability Studies on in Vitro Blood-Brain Barrier Models; Physiology, Pathology, and Pharmacology, Cellular and Molecular Neurobiology, 2005, 25: 59-127.
Wang, et al., Mining a yeast library for brain endothelial cell-binding antibodies, Advance Online Publication, Nature Methods, 2007, p. 1-3, Advance Online Publication.
Shusta, E.V., Towards Representative in Vitro Blood-Brain Barrier Models, Department of Pathology and Laboratory Medicine, University of Wisconsin, Apr. 2005.
Weidenfeller C., Svendsen C.N., Shusta E.V., Interaction of Brain Microvascular Endothelial Cells and Neural Progenitor Cells, VIth Conference on Cerebral Vascular Biology, Muenster, Germany, Jun. 2005.
Calabria A.R., Weidenfeller C., Shusta E.V., "Strategies for Improving in Vitro Blood-Brain Barrier Models", Biochemical Engineering XIV, Harrison Hot Springs, Canada, Jul. 2005.
Wang et al., "Distinct efficacy of pre-differentiated versus intact fetal mesencephalon-derived human progenitor cells in alleviating rat model of Parkinson's disease", International Journal of Developmental Neuroscience, 2004, 22:175-183.
Shen et al., "Endothelial Cells Stimulate Self-renewal and Exapand Neurogenesis of neural Stem Cells", Science, 2004, 304:1338-1340.
Stanness et al., "A New Model of the Blood-Brain Barrier: co-culture of neuronal, endothelial and glial cells under dynamic conditions", NeuroReport, 1999, 10:3725-3731.
Gaillard et al., "Establishment and functional characterizations of an in vitro model of the blood-brain barrier, comprising a coculture of brain capillary endothelial cells and astrocytes", Pharmaceutical Sciences, 2001, 12:215-222.
Keep RF, "Neural Progenitor cells and blood-brain barrier modeling", Journal of Neurochemistry, 2011 (accepted manuscript).
Eaton et al., "Autocrine BDNF secretion enhances the survival of serotonergic differentiation of raphe neuronal precursor cells grafted into the adult rat CNS", Experimental Neurology, 1996, 140:105-114.
Eaton et al., "Developmental regulation of early serotonergic neuronal differentiation: the role of brain-derived neurotrophic factor and membrane depolarization", Developmental Biology, 1995, 170:169-182.

* cited by examiner

*Primary Examiner* — Laura Schuberg
(74) *Attorney, Agent, or Firm* — Quarles & Brady, LLP

(57) ABSTRACT

A method of creating a multicellular blood-brain barrier model is disclosed. In one embodiment, the method comprises culturing primary brain microvascular endothelial cells or embryonic stem cell-derived endothelial cells upon a permeable support in the presence of neural progenitor cells.

9 Claims, 7 Drawing Sheets

BLOOD-BRAIN BARRIER MODEL

CROSS-REFERENCE TO RELATED APPLICATIONS

This application is a divisional application of U.S. application Ser. No. 11/766,633 filed Jun. 21, 2007, which claims the benefit of U.S. Ser. No. 60/816,033 filed Jun. 23, 2006. Both applications are incorporated by reference herein.

STATEMENT OF FEDERALLY SPONSORED RESEARCH OR DEVELOPMENT

This invention was made with government support under AA013834 and NS052649 awarded by the National Institutes of Health. The government has certain rights in the invention.

BACKGROUND

The blood-brain barrier (BBB) is composed of a specialized class of endothelium that forms a cellular barrier between the bloodstream and the interstices of the adult brain. By restricting non-specific flux of blood-borne constituents, the BBB plays an important role in maintaining parenchymal homeostasis, and strictly regulates transport of ions, small molecules, proteins, and cells into and out of the brain. The BBB accomplishes these tasks because its unique endothelium is endowed by epithelial-like tight junctions joining adjacent endothelial cells, lacks fenestrae, and possesses a rich array of molecular transport systems. Although the endothelium is the principle determinant of barrier function, perivascular non-endothelial cells in the local microenvironment have been shown to make significant contributions. Astrocytes (Stewart and Wiley 1981; Risau et al. 1986b; Janzer and Raff 1987), neurons (Tontsch and Bauer 1991) and pericytes (Balabanov and Dore-Duffy 1998; Ramsauer et al. 2002) have all been demonstrated to provide cues that result in the unique BBB endothelial phenotype.

Although the inductive properties of the aforementioned brain cell types have been confirmed through a multitude of in vivo and in vitro studies, the cell type(s) responsible for early embryonic BBB induction have not been distinguished. The developmental timecourse of embryonic BBB formation differs between species, but it is generally well accepted that the onset of BBB development begins prenatally and is followed by a gradual maturation to full BBB function (Bauer and Bauer 2000; Engelhardt 2003). For example, in rodents, vascular fenestrae disappear, pinocytosis decreases, and vessels decrease in diameter between embryonic days E11 and E17 (Bauer et al. 1993; Stewart and Hayakawa 1994; Bolz et al. 1996). The onset of tight junction formation is detectable from day E15, and tight junctions continue to increase in complexity through postnatal day P1 (Butt et al. 1990; Schulze and Firth 1992; Bauer et al. 1995; Kniesel et al. 1996; Nico et al. 1999). During this time, the transendothelial electrical resistance (TEER) of pial vessels is intermediate between peripheral vessels and the adult BBB (Butt et al. 1990; Schulze and Firth 1992; Bauer et al. 1995; Kniesel et al. 1996; Nico et al. 1999). A combination of the aforementioned attributes serves to restrict passage of protein into the embryonic brain (Risau et al. 1986a; Bauer et al. 1995; Dziegielewska et al. 2000), while a gradual decrease in BBB permeability to small tracers such as inulin and sucrose begins during embryonic development and continues postnatally (Ferguson and Woodbury 1969). Finally, transporter expression at the BBB also evolves from embryonic to postnatal stages as a result of changing nutritional needs (Johanson 1989; Gerhart et al. 1997).

The early embryonic developmental timecourse for the BBB raises the question as to what inductive factors or cell types drive the endothelial differentiation process. As mentioned above, astrocytes have long been linked with induction of BBB properties by in vitro and in vivo experiments (Stewart and Wiley 1981; Risau et al. 1986b; Janzer and Raff 1987). However, angiogenic vessels invade the immature embryonic neural environment and begin establishing BBB characteristics well in advance of the onset of gliogenesis as defined by the presence of GFAP-positive astrocytes in rodent brain (E18, (LeVine and Goldman 1988)). In addition, the developing BBB vessels have little extracellular matrix with few astrocyte contacts even just days prior to birth (Caley and Maxwell 1970). In fact, for rodents, much of the astrocyte generation takes place postnatally during which time the astrocyte sheath that surrounds mature brain capillaries is developed (Johanson 1989). Therefore, it is unlikely that astrocytes function in the early BBB induction process, but instead other cell types may be responsible for the early onset of BBB properties.

NPC are a major cell type in the developing embryonic brain, and it was recently reported that the differentiation and morphology of NPC are influenced by endothelial cells (Shen et al. 2004). In co-culture with endothelial cells, NPC show reduced neurogenesis and elevated self-renewal (Shen et al. 2004). Neural progenitors have also been observed in contact with early postnatal blood vessels, and this was implicated as an early stage in astrocyte differentiation (Zerlin and Goldman 1997). In addition, when endothelial cells and neural stem cells are grown in direct contact, it was shown that the adult neural stem cells could even produce progeny that exhibited an endothelial phenotype (Wurmser et al. 2004). Finally, adult neural stem cells are often found localized in perivascular spaces of the brain such as the subventricular zone and hippocampus, and it is thought that the vasculature is an important part of the stem cell niche (Doetsch 2003b).

Given the cellular interplay in the endothelial cell to NPC direction, we examined herein whether NPC could also influence brain endothelial cell phenotype. In this specification, we demonstrate that NPC isolated from the E14 embryonic brain induced BBB properties in an in vitro model consisting of primary rat brain microvascular endothelial cells in co-culture with NPC. We disclose an improved BBB model and method for examining the permeability of the BBB to test compounds.

BRIEF SUMMARY OF THE INVENTION

In one embodiment, the present invention is a method of creating a multicellular blood-brain barrier model, comprising the step of culturing brain microvascular endothelial cells upon a permeable support in the presence of neural progenitor cells, wherein the cultured neural progenitor cells differentiate into mixtures of astrocytes, neurons, and oligodendrocytes such that a multicellular blood-brain barrier model is created.

In one embodiment the endothelial cells are isolated from mammalian brain capillaries. In another embodiment, the endothelial cells are derived from isolated embryonic stem cells.

In a preferred embodiment, the endothelial cells form a monolayer wherein the cells are confluent and express a preferable TEER of 20-50, most preferably 30-40 Ohm×cm$^2$, before exposure to the neuroprogenitor cells (NPCs) and greater than 100 Ohm×cm$^2$ after exposure to the neuroprogenitor cells (NPCs). In a most preferred embodiment, the TEER of the BBB is 100-250 Ohm×cm$^2$.

In one embodiment, the neural progenitor cells are isolated from mammalian cortices and are digested with ACCUTASE™ enzyme mixture. In one embodiment the neural progenitor cells are grown as free-floating neurospheres before exposure to the endothelial cells. In one embodiment, the neural progenitor cells are pre-differentiated before exposure to endothelial cells. In one embodiment the neural cells are removed after the endothelial cells are confluent and express a TEER greater than 100 Ohm×cm$^2$.

The invention is also a blood-brain barrier model comprising at least three components within a liquid-containing vessel. The first component comprises a confluent layer of brain microvascular endothelial cells or embryonic stem cell-derived endothelial cells, the second component comprises a permeable membrane support, wherein the first component forms a layer on the second component, and the third component comprises either (a) undifferentiated neural progenitor cells that are differentiated after contact with the first component to be a mixture of astrocytes, neurons and oligodendrocytes or (b) neural progenitor cells that have been pre-differentiated before contact with the first component to be a mixture of astrocytes, neurons and oligodendrocytes. The first and second components form a barrier between a top and a bottom chamber of the vessel and the third component is placed in the bottom chamber of the vessel. The third component may be in direct contact with the first and second component or may be separated by fluid.

Preferably the endothelial cells form a monolayer wherein the cells are confluent and express an initial TEER of 20-50, most preferably 35 Ohm×cm$^2$, before exposure to neuroprogenitor cells (NPCs). After exposure to neuroprogenitor cells (NPCs), most preferably the TEER is 100-250 Ohm×cm$^2$.

In one embodiment, one may construct the model described above and remove the neural cells after a TEER of greater than 100 Ohm×cm$^2$ has been obtained.

In another embodiment, the invention is a method of analyzing the blood-brain barrier permeability characteristics of a model compound, comprising the steps of exposing a model compound to the blood-brain barrier model and measuring the permeability of the barrier model to the compound.

Other features of the present invention will become apparent after review of the specification, claims and drawings.

DESCRIPTION OF INVENTION

In General

Figure 1:
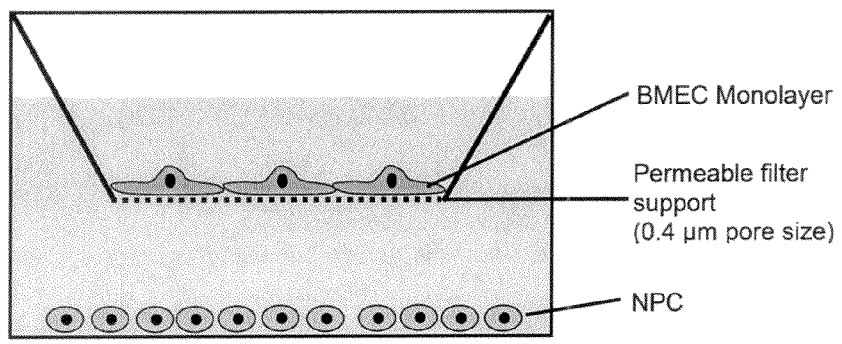
FIG. 1: In vitro model of the BBB. Primary BMEC were cultured for 2 days in the presence of puromycin to yield a nearly 100% pure BMEC monolayer on the collagen IV/fibronectin-coated filter support. On DIV 2 BMEC were switched to puromycin-free medium. After reaching confluence on DIV 3, NPC were added to the lower compartment in the presence or absence of mitogens (FGF-2, EGF). The resulting co-cultures were used to assess NPC effects on the BBB properties of the BMEC monolayer.

Accurate reproduction of the in vivo blood-brain barrier (BBB) in an in vitro setting has been a longstanding challenge in academia and the neuropharmaceutical industry. Issues of model quality include difficulty, purity, functionality, reproducibility, high throughput capacity, and accurate drug permeability prediction. To date, the most successful models usually include co-culture of primary brain microvascular endothelial cells (BMECs), which form the BBB in vivo, with primary brain astrocytes.

However, other brain cells such as neurons and neural progenitor cells have been shown to help govern in vitro BBB properties. This multicellular composite is known as the neurovascular unit. Unfortunately, current methods require the independent isolation of multiple cell types (astrocytes and neurons in particular) to try and reproduce the neurovascular unit in vitro, and the quality of these preparations invariably differs from experiment to experiment and from laboratory to laboratory.

Our approach to improving both the in vivo character as well as the reliability of in vitro BBB models is using embryonic neural progenitor cells (NPCs) as source tissue. Embryonic neuroprogenitor cells (NPCs) (nestin-positive) are easily isolated and expand rapidly for up to six weeks for rats and much longer for humans, leading to a large comparatively homogenous cell stock (Ostenfeld et al., 2002; Ostenfeld and Svendsen, 2003.) neuroprogenitor cells (NPCs) can be stimulated to differentiate into each of the major brain lineages, including astrocytes, neurons, and oligodendrocytes (Ostenfeld and Svendsen, 2003) Thus, from just one cell type (and isolation), many of the important BBB effector cells from the neurovascular unit can be simply generated as a mixed culture.

It is an advantage of the present invention that the relative percentages of the neurons and astrocytes can be controlled to create designer mixtures of brain cells that can be co-cultured with the brain microvascular endothelial cells. Several approaches can be used to tune the "brain side" of the co-culture model. Essentially, the timing after isolation from embryonic brains (time of expansion in culture without differentiation after isolation) influences the differentiation capacities of neuroprogenitor cells (NPCs). Early on (for example, 1 week [±1 day] for the rat cells) after isolation a higher ratio of neuroprogenitor cells (NPCs) differentiate into neurons while later induction of differentiation (for example, 4 weeks [±2 days] for rat cells) results in higher numbers of astrocytes (Ostenfeld and Svendsen, 2003).

In addition to this approach, chemical mediators can be used to direct the differentiation into the different NPC-derived cells. As nonexhaustive examples, bone morphogenic protein 2 drives the differentiation process towards glial fate and cyclic AMP is suitable for inducing the maturation (in vivo-like astrocyte) of astrocytes (Enkvist et al., 1996). In addition, to obtain higher neuron-containing cultures, retinoic acid can be used to trigger neuronal differentiation (Gallo et al., 2002). This is also possible by using mediators that trigger the Wnt signaling pathway (Katoh, 2002). Taken together, these methods can be used to "tune" the brain side of the co-culture model, thereby tuning the response of the BMEC monolayer.

The BBB model of the present invention performs admirably in terms of its permeability properties and outperforms astrocyte co-culture (see Examples). Also, as described above, the model is likely more reproducible given that each experiment can rely on the same NPC stock.

From an important practical perspective, we have shown that neuroprogenitor cells (NPCs) survive cryopreservation and elicit nearly identical properties after a preservation cycle. Therefore, an additional advantage of the present invention is the multiple uses of the same NPC stock over long periods of time.

In addition, the BBB model of the present invention can be manipulated to consist of larger populations of neuroprogenitor cells (NPCs) rather than mature cell types to represent more of the immature BBB found in the embryo or to yield an improved model in vitro system for the study of NPC-endothelial interactions. Such interactions may ultimately dictate the success of stem cell therapies given that neuroprogenitor cells (NPCs) lie in the vascular niche in the adult brain.

In summary, using neuroprogenitor cells (NPCs) as source tissue has the potential to revolutionize the in vitro BBB market by providing ease of use, reliability, and the most realistic in vivo-like properties to date.

Method of Creating a Model BBB

In one embodiment, the present invention is a method of creating a multicellular blood-brain barrier model, preferably using primary brain microvascular endothelial cells and neural progenitor cells as source tissues. One would typically begin by creating a culture of puromycin-purified primary brain microvascular endothelial cells (BMECs). In general, a suitable preparation is any monolayer of BMEC that is quite pure and possesses well developed tight junctions as well as expressing endothelial markers such as von Willebrand factor, PECAM-1, and p-glycoprotein. The Examples disclose the isolation of rat brain capillaries and the plating of the capillary cells on a permeable support. Although rat BMECs are specifically used in the Examples, one of skill in the art would understand that one could substitute other mammalian endothelial cells, most specifically other rodent cells and primate cells, including human cells using appropriate isolation and culture techniques (reviewed in Deli et al., 2005).

The BMEC monolayer is suitable for initiating a co-culture when the cells are confluent and express a TEER of 20-50, preferably greater than 35 Ohm×cm$^2$. This permeability measurement indicates an impermeability to ion diffusion characteristic of a confluent monolayer in the absence of co-culture. At this stage, BMECs express their typical spindle shaped morphology and form a monolayer without defects.

The permeable support is preferably situated in a commercially available TRANSWELL™ filter setup (or similar) that consists of an upper and lower chamber separated by a permeable membrane. FIG. 1 demonstrates a schematic version of a suitable apparatus.

In one version of the invention, cortical neural progenitor cells (NPCs) are isolated (preferably as described in the Examples) and disassociated into a single cell suspension. (Although rat neuroprogenitor cells (NPCs) are specifically used in the Examples, one of skill in the art would understand that one could substitute other mammalian cells, most specifically other rodent cells and primate cells, including human cells.) The cells are seeded, preferably at a density of $2\times10^5$ cells/ml in NPC culture medium along with epidermal growth factor, fibroblast growth factor and heparin (see Weidenfeller et al. 2007 and/or Example I for detailed preferred culture medium and approaches).

In one embodiment of the invention, cells are first grown as free-floating neurospheres and then co-cultured with the BMECs, preferably as described in the Examples.

A preferable co-culture of BMECs and neuroprogenitor cells (NPCs) is described at more length in the Examples. In brief, the neurospheres are preferably collected in vitro four days after isolation (DIV 4) and enzymatically treated. The cells are then counted and plated in a lower compartment of the TRANSWELL™ filter system with medium allowing NPC differentiation. Although the Example shows cells plated at the bottom of the lower compartment of the TRANSWELL™ filter system, the neuroprogenitor cells (NPCs) could also be grown in direct contact with the BMECs. This could be by, for example, growing the neuroprogenitor cells (NPCs) on the reverse side of the TRANSWELL™ filter itself.

In another embodiment of the present invention, the neuroprogenitor cells (NPCs) are pre-differentiated before combination with the BMECs. By 8 days the pre-differentiated cells no longer display the expression of nestin, the NPC marker. Populations of cells expressing GFAP (astrocytes), β-tubulin (neurons), and myelin basic protein (oligodendrocytes) are present. Example II is an example of an embodiment of the present invention in which the neuroprogenitor cells (NPCs) are pre-differentiated for 6-14 days. While twelve days is a preferred pre-differentiation time, Applicants note that the present invention is suitable for neuroprogenitor cells (NPCs) that are pre-differentiated, preferably between 6 and 14 days or under conditions that allow substantial differentiation into astrocyte and neuronal mixtures to occur.

After co-culture of BMECs and neuroprogenitor cells (NPCs), one may wish to obtain a TEER measurement of the resulting BBB. Preferably, the TEER will be greater than 100 Ohm×cm$^2$. The Examples below show TEER measurements at 100-120 Ohm×cm$^2$.

We envision that one may wish to pre-differentiate the neuroprogenitor cells (NPCs) for a varied number of days and under various conditions depending on the in vitro model needed. Early on after predifferentiation there are still nestin-positive cells in this in vitro system resulting in a four cell system together with the astrocytes, neurons, and BMECs as a model for early development with early induction properties. When pre-differentiated for a longer time (for example, 8-14 days for the rat), nestin-positive cells fully differentiate into astrocytes and neurons resulting in a more adult-like in vitro system capable of maintaining high TEER and improved BMECs permeability properties for a longer period of time. In addition, as described earlier, various cofactors (bone morphogenic protein, retinoic acid, cyclic AMP) can be added to the differentiation medium to help tune the ratios of the different cell types. After one has co-cultured BMECs and pre-differentiated neuroprogenitor cells (NPCs), one may wish to take a TEER measurement. Preferably, this measurement will be over 100 Ohm×cm$^2$. Applicants envision that one will obtain TEERs of 150, 200, or preferably 250 Ohm×cm$^2$ upon optimization using factors described above and below in this specification.

The puromycin purification step is important (but not required). One of skill in the art would understand that puromycin may be substituted by other toxins such as vincristine, vinblastine, colchicine that are recognized by the efflux transport system of the brain endothelial cells.

In one embodiment of the invention, the method is performed with primary rat BMECs and embryonic rat cortical neuroprogenitor cells (NPCs). However, one of skill in the art would understand that other mammalian cell species are substitutable. Additionally, one may wish to create a hybrid barrier with rat/human or human/non-human primate components.

Human nestin-positive cells would be treated similarly to the treatment described for rat nestin-positive cells in the Examples. An important exception is that human neurospheres are passaged every 14 days by sectioning into 200-μm sections prior to seeding into fresh growth medium. The isolation and culture of human endothelial cells would be performed similarly to that described for rat BMECs, using instead human autopsy brain tissue from which the capillaries are isolated.

For cultures based on species other than rat and human, the culture conditions (growth factors and time in culture) have to be adjusted according to the best induction of BBB properties (expression of specific marker proteins, high TEER and low permeability).

In another embodiment of the invention, one would substitute the primary BMECs described above with embryonic stem cell-derived endothelial cells (ECs). ECs can be derived from embryonic stem cells with reasonably high yield and purity (Kubo et al., 2005; Kaufman et al., U.S. Pat. No. 7,176,023) and would provide an unlimited supply of ECs that would avoid the isolation of adult BMECs. This would clearly be an advantage for a human BBB model, where reliance on autopsy tissue would be removed. The embryonic ECs that are essentially naïve in that they have not been exposed to the brain microenvironment would be cultured with either neuroprogenitor cells (NPCs) or pre-differentiated neuroprogenitor cells (NPCs) to induce BBB properties and complete the in vitro BBB model. One familiar with the art would also understand that adult NPC could be used in replacement of embryonic NPC.

BBB Model

In another embodiment, the present invention is an in vitro blood-brain barrier model comprising three components within a liquid-containing vessel. The first component is a confluent layer of brain microvascular endothelial cells, as described above. The second component is a permeable membrane support, preferably the TRANSWELL™ permeable filter support (pore size 0.4 μm) described in the exhibits. For permeability studies with higher molecular weight components (antibodies, phage), the pore sizes can be adjusted (1-3 μm filters are available). Also suitable would be hollow fibers, side-by-side chambers, and different pore density or pore size filers. The third component comprises either pre-differentiated neural progenitor cells or undifferentiated embryonic neural progenitor cells that are co-cultured with BMECs. After co-culture, one could remove the NPC or NPC-derived cells and retain good BBB characteristics for a period of time. See FIG. 1 for a preferable model. The first and second components are a permeable barrier between a top and bottom section of the vessel. Typically, the vessel is filled with culture medium as described in Examples I-III (NPC culture medium [DMEM:HAMS-F12 at 3:1 supplemented with B27 (2% v/v), epidermal growth factor (EGF, 20 ng/mL) fibroblast growth factor (FGF-2, 20 ng/ML), and heparin (5 μg/mL)].

The embryonic neural progenitor cells that are co-cultured with the BMECs having the characteristic cellular distributions presented, (FIG. 4) will yield a BBB model having early inductive characteristics. Pre-differentiated embryonic neural progenitor cells could have a variety of cellular distributions for astrocytes, neurons, and oligodendrocytes that will all yield improved BBB model characteristics. The methods described in Example II, FIG. 8 yield one such combination that outperforms simple astrocyte culture.

In one embodiment, one may construct the model described above and remove the neural cells after a TEER of greater than 100 Ohm×cm² has been obtained.

Additionally, a suitable BBB has particular permeability characteristics that are useful in a BBB model. The Examples demonstrate specific characteristics. For example, Example I describes the effects of neuroprogenitor cells (NPCs) on BMEC morphology and improved tight junction fidelity. In addition, Examples describe the improvement in impermeability by TEER measurement. The TEER measurements are often in the range of 100-120 Ohm×cm². This range allows significant improvement in small molecule permeability measurements and is also regarded as a suitable permeability range by researchers experienced in the art. Similarly, Example II indicates the improved permeability of BBB models using pre-differentiated neural progenitor cells that also performs better than astrocyte co-culture, the current state-of-the-art. Applicants envision that with optimization, TEER measurements using pre-differentiated neural progenitor cells will improve to 150 Ohm×cm², 200 Ohm×cm² or most preferably 250 Ohm×cm².

In another embodiment of the invention, the first component comprises differentiated embryonic stem cells that have been differentiated into endothelial cells. A suitable BBB model will have characteristics described above for the primary BMEC derived blood-brain barrier.

One may also wish to manipulate the components of the BBB model to create a membrane that is more suitable for an individual study. For example, one may wish to manipulate the cell population so that the model will more clearly mimic the BBB from different parts of the brain. Using neuroprogenitor cells (NPCs) derived from different regions of the brain can result in different astrocyte—neuron ratios (Ostenfeld et al., 2002) and the resultant brain cells will likely have regional specificity in terms of their BBB-inductive properties. Also, as described earlier, the use of undifferentiated versus pre-differentiated neuroprogenitor cells (NPCs) can be used to tune the BBB model for specific applications ranging from embryonic drug delivery to stem cell transplantation. As a further example, using different substrates for both the BMECs and neural progenitor cell components (different pore sizes and extracellular matrix coatings) or even growing the BMECs and neural progenitor cells in direct contact to form capillary like structures can lead to BBB models that can be used to investigate a variety of pharmacologic, toxicologic, and developmental phenomena. Monitoring characteristics that are critical for representing the in vivo situation (high TEER, expression and polarization of transporters like the p-glycoprotein drug efflux transporter and the GLUT1 glucose transporter, expression and maintenance of well-developed tight junctions) would help determine the appropriate approach for a particular application.

Use of the Model BBB to Analyze Compounds.

One would wish to use the model BBB of the present invention to analyze permeability characteristics of various test compounds. Most preferably one would analyze the compound in the following manner:

Many methods can be used to determine BBB permeability as well as uptake and efflux rates using an in vitro model. As an example, the rates for trans-BBB transport can be used to directly determine a pseudo steady-state permeability value (Pe) which is an estimate of in vivo permeability for a particular pharmaceutical compound, protein, or drug carrier. With the assumption that the concentration in the upper fluid compartment is static, and with a correction for the resistance provided by the membrane itself, the permeability can be readily determined for each test compound. Briefly, the transcytosis rate (Q) can be divided by the concentration of material added to the apical chamber (Ca) and the area of the membrane (Am) to yield a total permeability (Pt) that includes resistances due to the monolayer and the membrane (Pt=Q/[AmCa], or using clearance volume terminology Pt is equal to the slope of the clearance volume versus time line divided by the membrane area). Subsequently, Pe can be calculated by correcting for the resistance supplied by the cell free membrane (Pm) (1/Pe=1/Pt−1/Pm) (Bickel, U. How to measure drug transport across the blood-brain barrier. *NeuroRx* 2005, 2, 15-26.). This strategy was used successfully to determine the transcytosis rate of fluorescein and its associated permeability (Pe=3.3×10-4 cm/min) through the in vitro model as demonstrated in Example I.

EXAMPLES

Example I

Differentiating Embryonic Neural Progenitor Cells Induce Blood-Brain Barrier Properties Materials and Methods Isolation of Rat Brain Microvessel Endothelial Cells The isolation of rat brain capillaries was performed as previously described (Weidenfeller et al. 2005; Calabria et al. 2006). Briefly, the meninges-free cortices from adult male Sprague Dawley rats (220-250 g) were mashed with forceps, and thoroughly triturated. Capillaries were separated from surrounding tissue by sequential digestion/density centrifugation steps with type 2 collagenase (Worthington Biochemical Corporation) and Collagenase/dispase (Roche Applied Science). The capillaries were plated onto 1.12 cm² TRAN- SWELL-CLEAR™ filter permeable supports (0.4 μm pore size, Corning) coated with collagen IV/fibronectin in puromycin-supplemented medium (4 μg/mL) containing DMEM, 20% bovine platelet poor plasma derived serum, 1 ng/mL human basic fibroblast growth factor (FGF-2/bFGF, R&D Systems), 1 μg/mL heparin, 2 mM L-glutamine, and an antibiotic-antimycotic solution (Penicillin-Streptomycin-Amphotericin (PSA): 100 U/mL penicillin, 100 μg/mL streptomycin, and 0.25 μg/mL amphotericin). Cultures were maintained in a 37° C. incubator under humidified 5% $CO_2$/95% air.

Isolation and Culture of Rat Cortical Embryonic Neural Progenitor Cells

Rat cortical NPC were isolated as described previously (Ostenfeld et al. 2002). The cortices were dissected from E14 rat brains. The tissue was treated with Accutase™ (Innovative Cell Technologies, San Diego, Calif., USA) for 10 minutes at 37° C., washed twice in DMEM, and then dissociated into a single cell suspension. Cells were initially seeded at a density of $2 \times 10^5$ cells/ml in a T25 flask in defined serum-free NPC culture medium [DMEM:HAMS-F12 at 3:1 supplemented with B27 (2% v/v), epidermal growth factor (EGF, 20 ng/ml), fibroblast growth factor (FGF-2, 20 ng/ml), and heparin (5 μg/ml)]. Cells were grown as free-floating neurospheres for 3 days and then used for co-culture with BMEC on day in vitro 4 (DIV4).

Isolation of Astrocytes

Cortices from neonatal rats (P6) were minced in a petridish containing ice-cold Hanks' Balanced Salt Solution (HBSS). The minced tissue was centrifuged for 2 min (500 g), resuspended in HBSS containing trypsin (0.5 mg/ml) and incubated at 37° C. for 25 min in a shaker bath. The trypsinized tissue was triturated and the cell suspension was filtered through a 70 μm mesh. $3 \times 10^4$ cells/$cm^2$ were plated in DMEM containing 10% FBS, 10% horse serum, 2 mM L-glutamine, and PSA. Medium was changed every third day and cells were treated with 0.25 mM dibutyryl cAMP for 3 days prior to co-culture with BMEC to induce an in vivo-like phenotype (Segovia et al. 1994; Enkvist et al. 1996). The presence of GFAP-expressing astrocytes was confirmed by immunocytochemistry.

Co-Culture of BMEC with NPC or Astrocytes

Neurospheres were collected on DIV4, treated with ACCUTASE™, and washed twice in DMEM. Live cells were counted on a hemacytometer, and $2.5 \times 10^5$ NPC/$cm^2$ were plated in the lower compartment in either mitogen-free medium allowing NPC differentiation (DMEM:HAMS-F12 at 3:1, 2% v/v B27, 1% FBS, and PSA, with poly L-lysine/laminin coating) or with mitogen-containing medium to suppress differentiation (mitogen-free medium plus 20 ng/mL EGF and 10 ng/mL FGF-2, without poly L-lysine/laminin coating) (Ostenfeld et al. 2002). The TRANSWELL™ filter containing the confluent BMEC was then added to complete the co-culture system (FIG. 1). Mitogen-mediated suppression of NPC differentiation in the presence or absence of BMEC was confirmed by anti-nestin, anti-GFAP and anti-βIII tubulin staining. In this way, it was determined that the NPC populations were GFAP and βIII tubulin negative prior to and after BMEC co-culture in mitogen-containing medium. NPC densities up to $1 \times 10^6$ NPC/$cm^2$ were tested, but were not found to yield any increases in TEER induction above that seen with the $2.5 \times 10^5$ NPC/$cm^2$ plating density. Embryonic mouse fibroblasts (3T3, ATCC) were used as a non-neural co-culture control.

One day prior to co-culture, astrocytes were preconditioned in mitogen-free medium to avoid effects that serum withdrawal could have on the temporal response of astrocyte induction. After 24 hours of preconditioning, astrocytes were treated with trypsin-EDTA solution and single cells were resuspended in mitogen-free medium. A total of $6.25 \times 10^4$ astrocytes/$cm^2$ were added to the lower compartment in mitogen-free medium, and the filter insert with the confluent BMEC monolayer was added.

Immunocytochemistry

All steps were performed at 20° C. The BMEC and NPC cultures were gently washed three times with 0.01 M PBS and fixed with paraformaldehyde (4% w/v in PBS). After blocking and permeabilization (10% goat serum containing 0.1% Triton X-100 in PBS (PBSG), 30 min), primary antibodies (anti-nestin, [BD Biosciences], rabbit anti-glial fibrillary acidic protein [GFAP, DAKO Cytomation], anti-βIII tubulin [BD Biosciences], anti-von Willebrand factor [Sigma], anti-occludin, anti-zonula occluden-1, mouse anti-claudin 5 [Invitrogen], primary antibody mix for MBP and CNPase detection [Orion Biosolutions]) were diluted in PBSG with 3% goat serum and incubated with samples for 1 h. Samples were washed with PBS and incubated with secondary antibodies (Texas Red goat anti-rabbit IgG, Alexa Fluor goat anti-mouse IgG antibody) diluted in PBSG with 3% goat serum for 1 h. DAPI nuclear stain at a concentration of 300 nM in PBS was added to the wells for 5 min. For immunocytochemistry of brain tissue sections, freshly isolated E14 rat brains were embedded in tissue freezing medium, snap frozen in liquid nitrogen, sectioned, and labeled as described above.

Resistance measurements Transendothelial electrical resistance (TEER) was measured using an EVOM voltohmmeter (World Precision Instruments). Resistance values ($\Omega \times cm^2$) were corrected by subtracting the resistance of a substrate coated, empty filter. At each time point, three TEER measurements were taken per TRANSWELL-CLEAR™ filter to yield an average TEER value for each filter. Subsequently, TEER values for triplicate filters at each culture condition were used to compute the mean and standard deviations reported.

Permeability Studies

The permeability was assessed by determining the flux of fluorescein through the BMEC monolayer. Fluorescein sodium salt in DMEM was added to the apical filter compartment to produce a uniform initial concentration of 1 μM. Subsequently, 200 μl were removed from the basolateral compartment after 0, 15, 30, 45, and 60 min. The fluorescence was measured with the FLx800 fluorescence reader (Bio-Tek Instruments) and the rates of fluorescein accumulation in the lower compartment used to determine the permeability as described previously (Perriere et al. 2005).

Quantitative Analysis of Cultures

Counting of NPC-derived cell types was performed by overlay of anti-nestin (undifferentiated NPC), anti-βIII tubulin (neurons), and DAPI images or by overlay of anti-nestin, anti-GFAP (astrocytes), and DAPI images. The cell distribution was assessed by determining the percentage of cells positively-labeled for a particular marker. For this determination, 5 random fields for each type of labeling (βIII tubulin/Nestin or GFAP/Nestin, ~1000 total cells each condition) were counted at a magnification of 40×. Proliferation of BMEC was evaluated by BrdU incorporation with the 5-Bromo-2'-deoxy-uridine Labeling and Detection Kit I (Roche Applied Science) according to the manufacturer's instructions. BrdU was added to the cultures at the beginning of the 24 h co-culture of BMEC with NPC. The cells were fixed after 24 h, total BMEC numbers were assessed by DAPI nuclear stain, and the percentage of BMEC incorporating BrdU was determined for 6 different fields on each of 3 filters (800 cells for each condition). An analogous procedure was used to assess NPC BrdU incorporation and total cell numbers of NPC. The percentage of BMEC containing frayed junctions over a significant fraction (greater than 10%) of their total cell border was determined by randomly choosing microscope fields in phase contrast mode where junctional ultrastructure is not visible. The immunocytochemical images for occludin labeling were then acquired in fluorescence mode. Junctions between adjacent cells (100 cells per image with 5 images total for each condition) were defined as frayed if immunolabeling illuminated tight junction protrusions that are not parallel to the cell-cell border.

Results

Primary Brain Endothelial Cell-Embryonic NPC Co-Culture Model

The influence of NPC on the barrier properties of adult BMEC was investigated using a novel in vitro model consisting of primary rat BMEC and embryonic rat cortical NPC. Since BMEC isolated from adult brains de-differentiate in vitro (Krizbai and Deli 2003), they have been widely used to study BBB induction and modulation, although they still possess some level of BBB properties. NPC and BMEC were co-cultured together using a microporous filter setup (TRANSWELL-CLEAR™ filter) with an upper compartment and a lower compartment representing the blood and brain side of the blood-brain barrier (BBB), respectively (FIG. 1). The filter setup allows the in situ measurement of the transendothelial electrical resistance (TEER) yielding information regarding the integrity of the BMEC monolayer by monitoring the paracellular flux of small electrolytes. Puromycin-purified BMEC were cultured on the upper surface of the filter membrane, and after 3 days in vitro (DIV3) had grown to confluence as determined by phase contrast microscopy. Puromycin treatment ensured a nearly 100% pure endothelial monolayer, and we and others have demonstrated that this rodent in vitro BBB model displays well defined tight junctions and forms an impermeable barrier to small molecule tracers (Perriere et al. 2005; Weidenfeller et al. 2005; Calabria et al. 2006). Importantly, the model has also proven reliable for the measurement of BMEC response to inductive factors such as cAMP, astrocytes, and glucocorticoids (Perriere et al. 2005; Weidenfeller et al. 2005; Calabria et al. 2006), and was therefore suitable for the testing of NPC inductive capacity. In order to co-culture NPC with the BMEC monolayer, freshly isolated NPC from E14 rats were expanded for 3 days in EGF and FGF-2 mitogen-containing medium (see Materials and Methods for details) and then cultured in the lower compartment such that the BMEC and NPC could interact via soluble mediators. When co-cultured in mitogen-free medium, NPC attached to the poly L-lysine/laminin coated substrate in the lower compartment, generating a mixture of NPC (nestin-positive) and differentiated progeny including astrocytes (GFAP-positive) and neurons (βIII tubulin-positive). Co-culture in the presence of mitogens supported solely proliferation as nestin-positive NPC.

NPC Influence on BMEC TEER and Permeability

Figure 2:
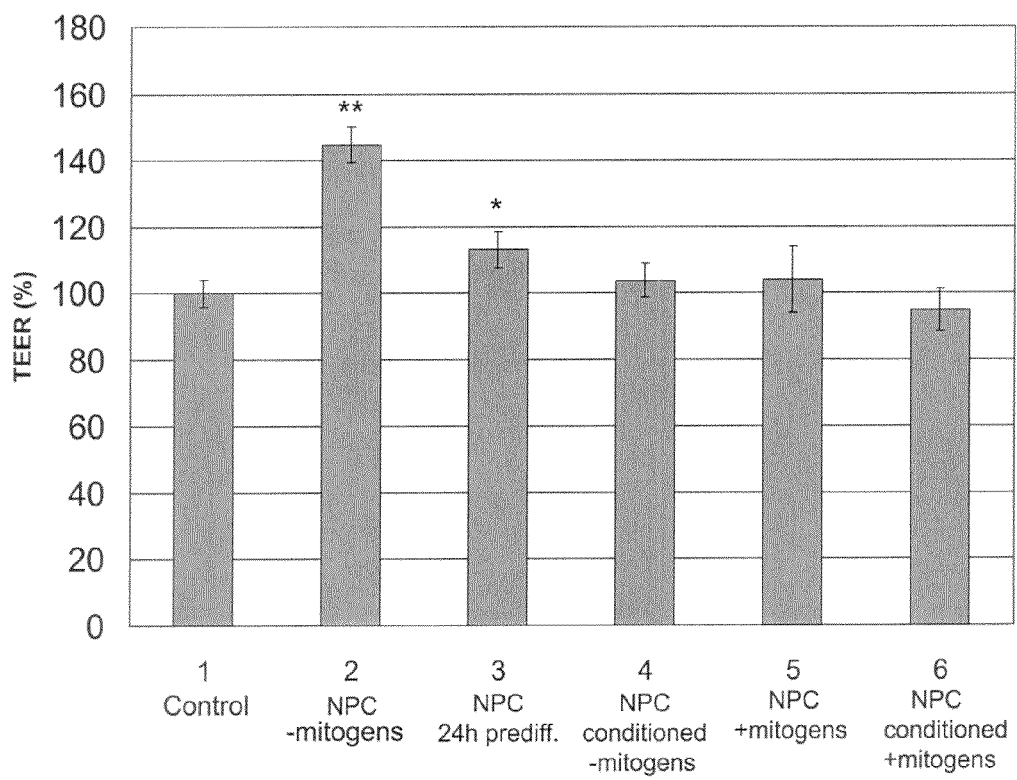
FIG. 2: Influence of NPC co-culture and NPC-conditioned media on BMEC TEER. BMEC were cultured as follows: 1. in the absence of NPC (control), 2. in the presence of differentiating NPC (+NPC −mitogens), 3. in the presence of 24 h pre-differentiated NPC (+NPC 24 h prediff), 4. in NPC-conditioned medium generated by 24 hour of NPC culture in mitogen-free differentiation medium (NPC conditioned −mitogens), 5. in the presence of NPC in mitogen-containing medium (NPC +mitogens), and 6. in 24 hour conditioned mitogen-containing medium from dividing NPC(NPC conditioned +mitogens). The TEER was monitored after 24 hours for each culture condition and expressed as normalized % of control TEER values. The mitogen-containing conditions (5 and 6) were independently normalized to a mitogen-containing BMEC monoculture control. The statistical significance is given with $p<0.001$ (**) and $p<0.03$ (*) as determined by the unpaired Student's t-test. Triplicate cultures were analyzed for each condition and results display mean±SD. The results are representative of 8 independent experiments where the increase in TEER in the presence of differentiating NPC (2) ranged from 17-53%.

The in vitro co-culture model was used to investigate a possible involvement of NPC in the induction of BBB properties in the BMEC monolayer. In order to determine whether NPC or NPC-derived cells could affect the in vitro barrier phenotype of BMEC monolayers, the TEER was measured in the presence or absence of differentiating NPC (mitogen-free conditions). TEER measurements after 24 hours of co-culture indicated a 47% increase in monolayer TEER with NPC (110±5 Ω×cm$^2$) when compared to control BMEC cultures lacking NPC (75±4 Ω×cm$^2$), indicating an early inductive response to soluble factors released by NPC (FIG. 2, columns 1 and 2). The barrier-enhancing effect in the presence of differentiating NPC was also observed in permeability studies where NPC co-culture reduced the monolayer permeability for fluorescein sodium salt by 33% with NPC influences (Table 1). This decrease in diffusion of the BBB-impermeable fluorescein directly correlated with the increase in TEER. In addition, to support the presence of soluble factors that mediate the increases in TEER, the medium conditioned by 24 hours of co-culture was serially applied to fresh BMEC monolayers. The BMEC-NPC co-culture conditioned medium again induced BMEC TEER (150±6%) compared with BMEC monolayers grown in medium conditioned by BMEC alone. Finally, even when NPC were maintained in an undifferentiated state for longer periods of 1-5 weeks in vitro prior to co-culture with BMEC, the induction properties were still observed under the mitogen-free conditions (31-43% increases in TEER).

In contrast, conditioned medium (24 h) from NPC differentiating in the absence of BMEC did not show an effect on the TEER within 24 h after application to BMEC (FIG. 2, column 4). When co-cultured with NPC that were pre-differentiated for 24 hours in the absence of BMEC, TEER increases were attenuated (11±6%) (FIG. 2, column 3). In order to determine whether proliferating, undifferentiated nestin-positive NPC or conditioned medium from proliferating, undifferentiated NPC can induce an increase in TEER, BMEC were co-cultured with NPC in the presence of mitogens or with NPC culture-conditioned medium from 24 hour mitogen-treated, proliferating NPC, respectively (FIG. 2, columns 5 and 6). No induction in BMEC TEER could be observed under these conditions after 24 h. Finally, the effects of non-neural embryonic 3T3 fibroblasts on BMEC were investigated and like the mitogen-treated NPC, no induction was observed (data not shown). The lack of induction in the presence of undifferentiated, proliferating NPC or 3T3 fibroblasts indicated that the simple presence of another cell type was not responsible for changes in phenotype observed in the presence of differentiating NPC.

Influence of NPC Co-Culture on BMEC Morphology

Figure 3:
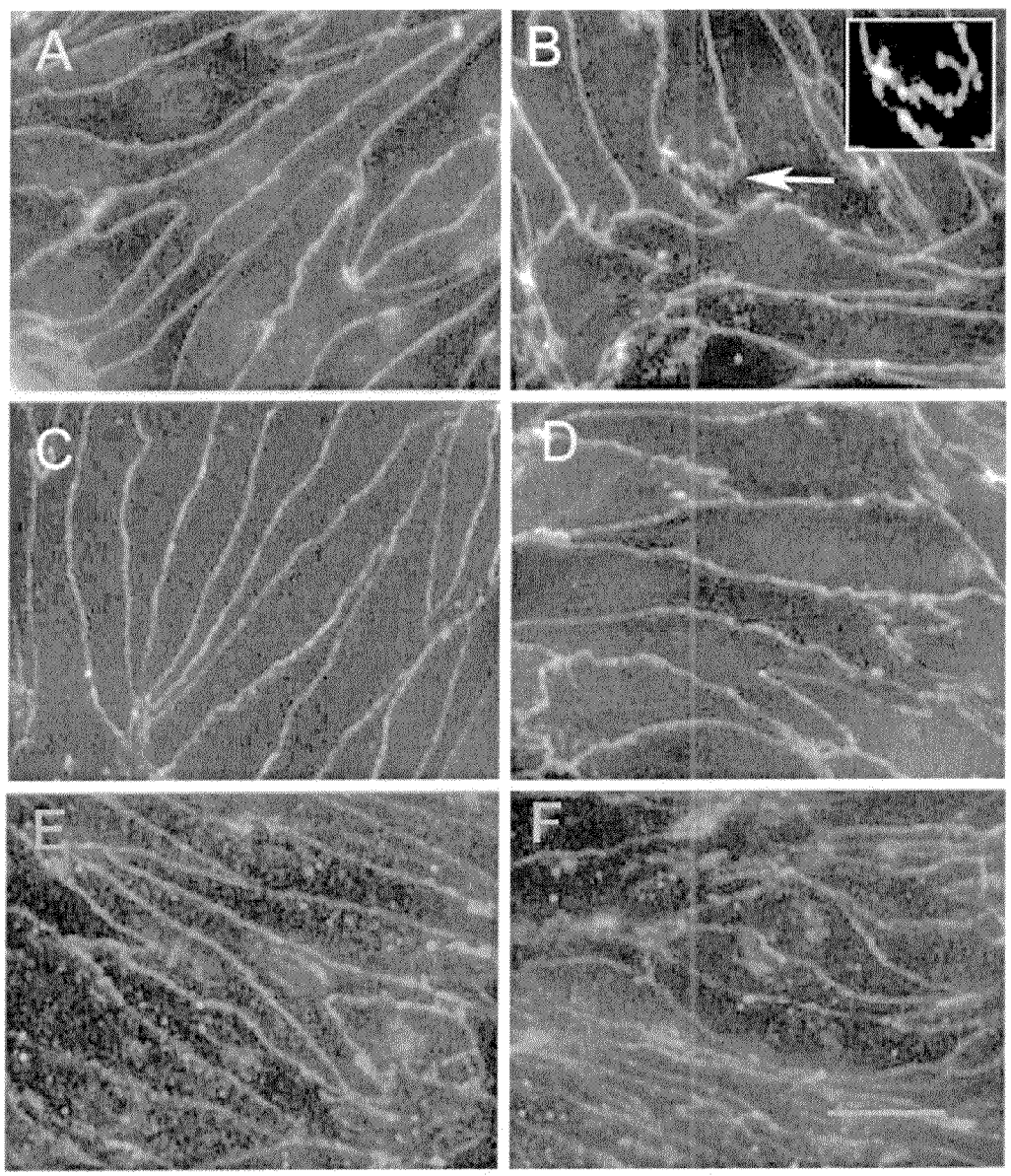
FIG. 3: Tight junction organization and cell morphology of BMEC in the presence (A, C, E) or absence (B, D, F) of differentiating NPC. After 24 hours of co-culture in mitogen-free medium, the BMEC were probed for ZO-1 (A, B), occludin (C, D) or claudin 5 (E, F). Note the tight junction protrusions perpendicular to the cell-cell borders that represent frayed junctions. An example denoted by the arrow is enlarged and shown in the inset of panel B. Representative fields are shown to illustrate the differences in junctional morphology. See Table 1 for the corresponding quantitative data. Scale bar represents 50 μm.

The tight junctions of BMEC cultured alone or co-cultured with NPC were investigated to determine if NPC were capable of influencing BMEC cell-cell contacts or cell morphology in a way that could account for the increased TEER and decreased fluorescein permeability. BMEC were probed with antibodies against tight junction proteins ZO-1, occludin, and claudin 5 in the presence (FIG. 3 A, C, E) or absence (FIG. 3. B, D, F) of differentiating NPC. In the presence of NPC the majority of the BMEC show well-established tight junctions and a distinct occludin, claudin 5, and ZO-1 staining. In the absence of NPC, cell-cell junctions were also evident, but tight junction staining indicated an irregular, frayed staining pattern in 65% of the BMEC while in the presence of NPC, only 34% of the BMEC exhibited such a junctional structure (Table 1, FIG. 3). The cell morphology and cell size were indistinguishable under these two conditions (Table 1). BMEC with or without NPC co-culture were probed for F-actin localization, and no difference between BMEC-NPC co-culture and BMEC monocultures was detected. In both cases, a strong peri-junctional actin localization together with intracellular actin filaments was observed (data not shown).

NPC Effects on BMEC Proliferation

Next, the filter density of BMEC was evaluated to determine whether or not the increased TEER values were the result of a tighter monolayer packing. BMEC monolayers with or without NPC co-culture were assessed using DAPI nuclear staining and 5-Bromo-2"-deoxy-uridine (BrdU) incorporation to investigate BMEC density and proliferation, respectively. As Table 1 indicates, no significant difference in the number of proliferating endothelial cells or BMEC cell density was observed between the NPC-BMEC co-cultures and BMEC mono-cultures.

Potential Inductive Cell Types in the Co-Culture System

Figure 4:
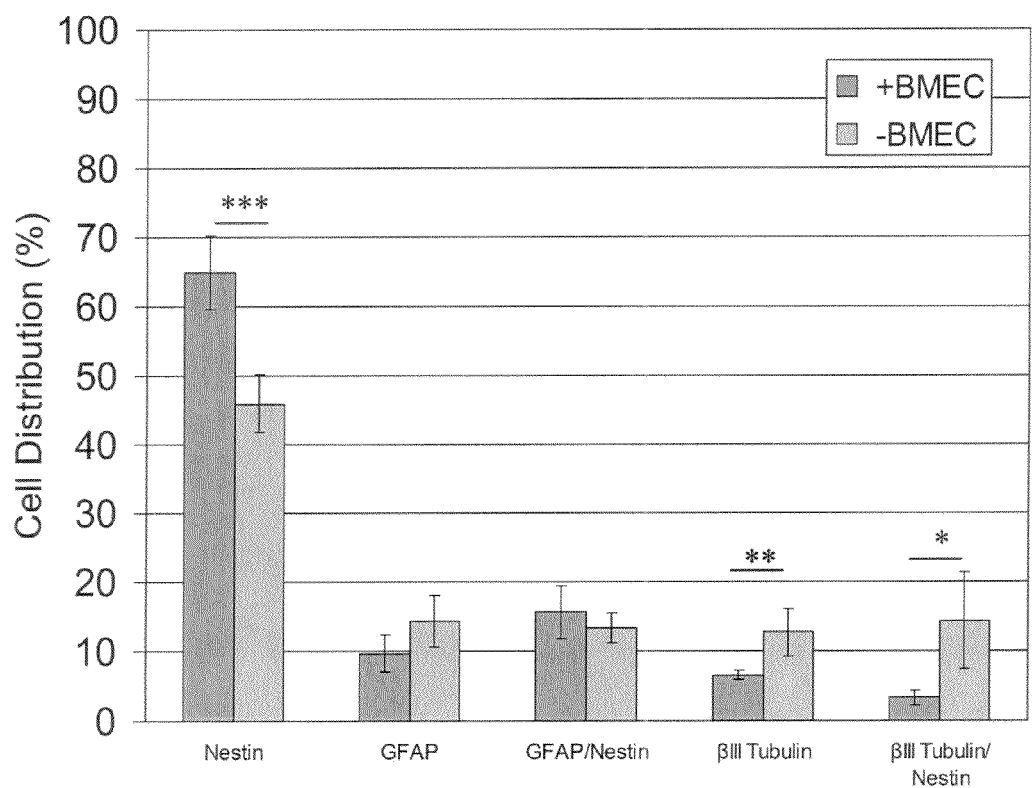
FIG. 4: Influence of BMEC on NPC differentiation. NPC were fixed 24 h after culture in presence or in absence of BMEC. Cell types were determined by indirect immunofluorescence using cell markers (βIII tubulin, GFAP, and nestin), and cells were counted. The statistical significance is given with $p<0.001$ (*), $p<0.01$ (), and $p<0.03$ (*) as determined by the unpaired Student's t-test. Results represent the means±SD of 5 different microscope fields (~1000 cells total).

In order to determine the NPC-derived cell types that might be responsible for the induction of TEER and the observed changes in junctional structure, NPC progeny in the basolateral compartment were probed for astrocytic (GFAP), neuronal (βIII-tubulin) and progenitor cell (nestin) markers (FIG. 4). There was no significant change in the total number of NPC-derived cells in the lower compartment with or without BMEC being present, and the number of proliferating BrdU$^+$ cells was also the same (~40%). The majority of NPC-derived cells remain nestin-positive (65±5.3%) after 24 hours in co-culture with BMEC during which time the NPC induction effects are first observed. Results also indicated that NPC differentiate into neuronal and glial cells. The second largest cell population was positive for both GFAP and nestin (15.6±3.8%) indicating that these cells are likely immature astrocytes. A small population (9.7±2.7%) of cells was solely GFAP-positive and considered to be more mature astrocytes. Very few neurons (6.5%±0.7%) and immature βIII tubulin- and nestin-positive neurons (3.3±1.0%) were generated in the presence of BMEC in the 24-hour timeframe. In the absence of BMEC, more NPC differentiated towards a neuronal fate while the numbers of solely GFAP-positive and GFAP/nestin co-stained cells remained unaffected. The increased number of neurons was accompanied by a lower number of nestin-positive cells in the absence of BMEC (46±4.2%), indicating a higher propensity for NPC to differentiate without BMEC influences. Oligodendrocytes were not detectable by immunofluorescence using antibodies against myelin basic protein or 2'3'-cyclic-nucleotide-3' phosphodiesterase (CNPase).

Effects of BMEC on NPC Morphology

Figure 5:
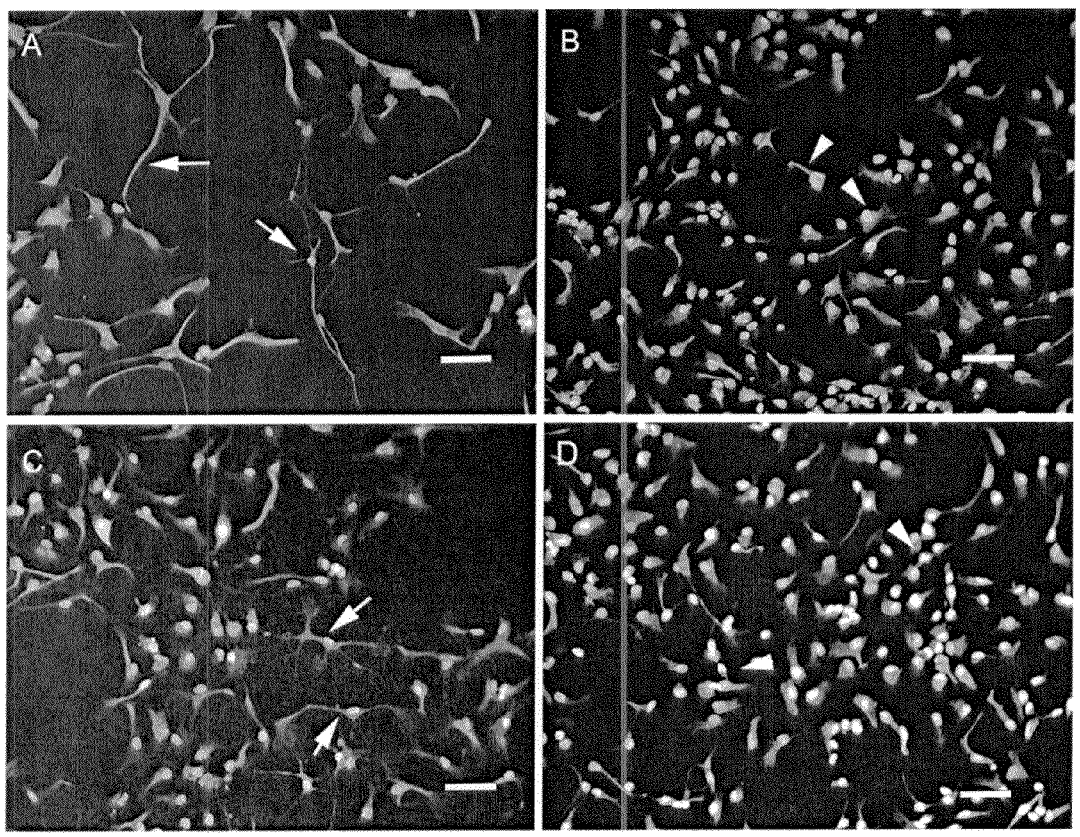
FIG. 5: Influence of BMEC co-culture on NPC morphology. Merged images of NPC that were probed for GFAP, nestin, and DAPI (panels A and B) or βIII tubulin, nestin, and DAPI (panels C and D). Panels A and C represent differentiation in the absence of BMEC and Panels B and D in the presence of BMEC. Arrows indicate small cell bodies and elongated thin processes (panels A and C) while arrowheads point to larger cell bodies and short processes (panels B and D). Scale bar represents 20 μm. Figures are shown in grayscale. For color figures see Weidenfeller et al, 2007.

Further evidence of BMEC-NPC crosstalk was gathered by investigating the influence of BMEC on the morphology of NPC-derived cell types. Co-culturing with primary BMEC significantly influences the morphology of the neural progenitor cells. NPC that were allowed to proliferate and differentiate (mitogen-free conditions) in the absence of endothelial cells possessed small cell bodies and displayed multiple thin processes typical of maturing astrocytes and neurons (FIGS. 5 A and C). In contrast, the number and length of processes is reduced in the presence of BMEC and the cells have a much more flattened precursor-like morphology (FIGS. 5 B and D). This effect was detectable for each of the astrocyte, neuron, and NPC cell types.

Determination of Blood Vessel-NPC Localization in E14 Rat Brain

Figure 6:
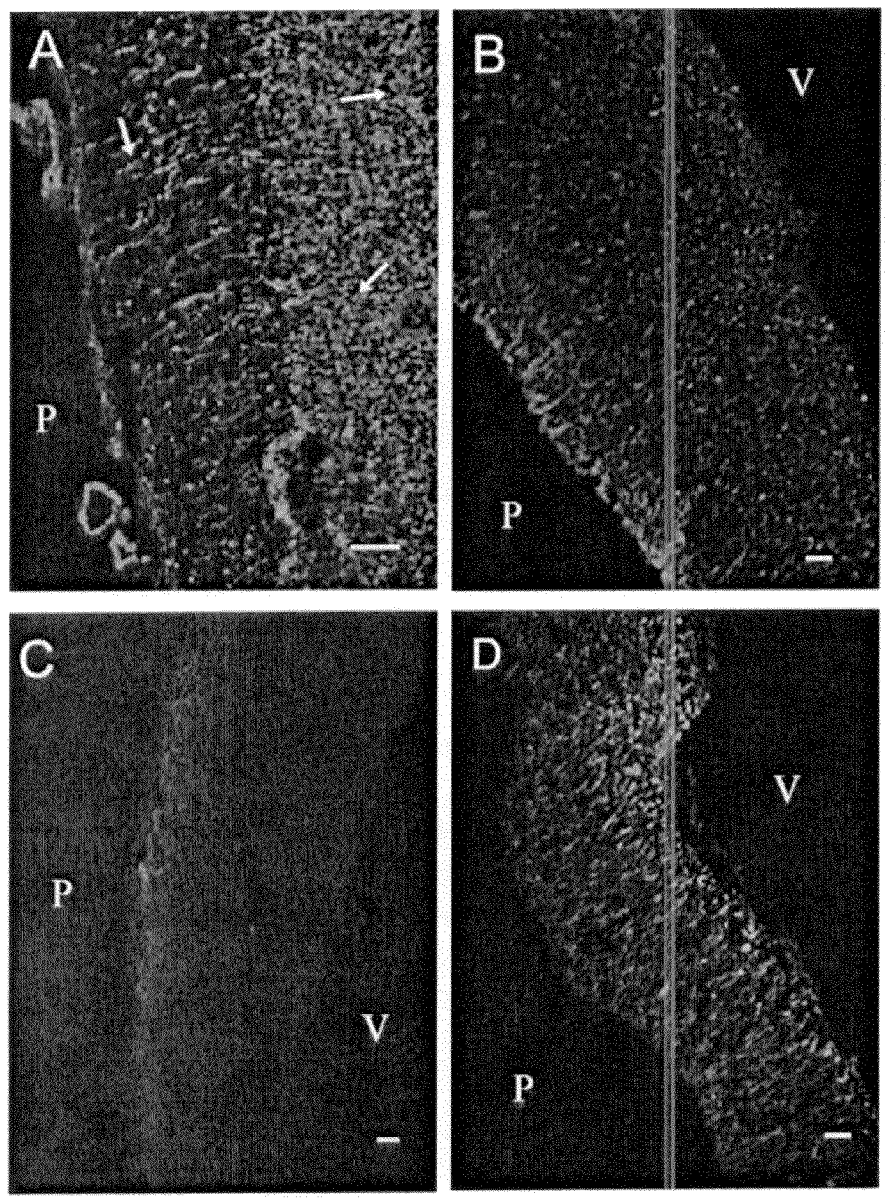
FIG. 6: Developing rat cortex at embryonic day E14. Panel A shows von Willebrand factor-positive blood vessels in the developing cortex. The vWF-positive vessels (several denoted by arrows) are localized in regions with large numbers of nestin-expressing cells and are distributed from the pial surface to the ventricle. Panel B indicates a highly βIII tubulin-positive region at the pial surface and homogenous distribution of neurons throughout the NPC-positive ventricular zone. Panel C again indicates the distribution βIII tubulin-positive neurons in addition to the absence of the tight junction protein occludin. Panel D illustrates that while the E14 rat cortex is highly nestin-positive, the astrocytic protein GFAP was not detected. P=pial surface; V=ventricle. Scale bar represents 400 μm. Figures are shown in grayscale. For color figures see Weidenfeller et al, 2007.

In order to correlate the in vitro results with the actual cellular distribution observed in vivo in the developing E14 rat cortex, the distributions of NPC, astrocytes, and neurons were investigated. NPC, as determined by nestin expression, could be identified throughout the whole cortex with a high density at the inner cortex close to the ventricle (FIG. 6 A, B, D). Radial glia spanned to the pial surface and were identified as elongated nestin-positive cells. In the pial-proximal area, a high density of neurons can also be observed (FIG. 6 B, C). Blood vessels could be easily identified throughout the embryonic brain by anti-Glut1, anti-PECAM1 and anti-von Willebrand factor labeling, and they were found in regions with high numbers of NPC and neurons (FIG. 6 A). In contrast, astrocytes were not detectable in the E14 rat cortex (FIG. 6 D). Finally, the tight junction protein occludin was not detectable indicating the presence of immature endothelial junctions in the E14 rat brain (FIG. 6 C).

Figure 7:
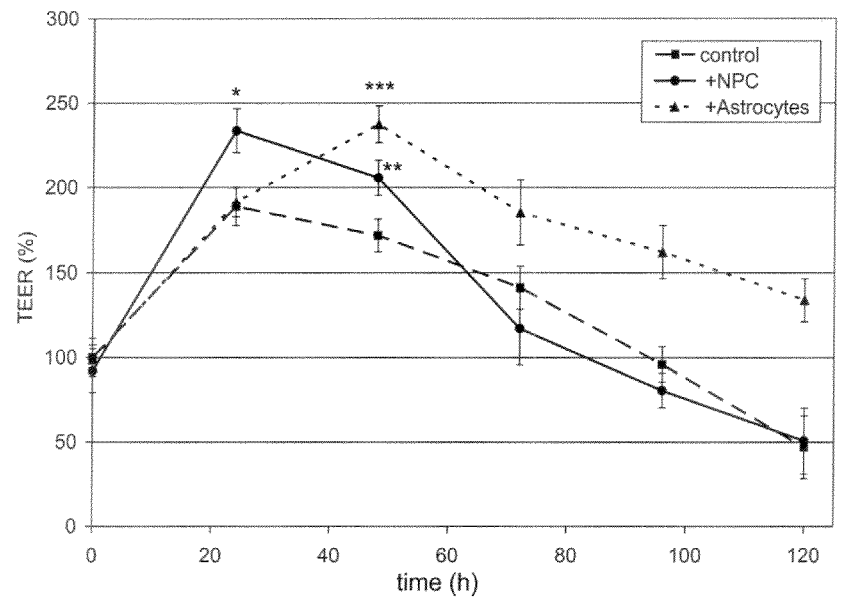
FIG. 7: TEER measurements of BMEC in co-culture with NPC or astrocytes. NPC or postnatal astrocytes were co-cultured with confluent BMEC using identical mitogen-free culture medium, and the TEER timecourse was followed for 5 days. Triplicate cultures were analyzed for each condition and the resistance measurements normalized to those of the untreated control at time zero, and results display mean±SD. Statistical significance between sample and control is indicated: $p<0.006$ (*), $p<0.02$ (), and $p<0.001$ (*). The results are representative of 5 independent co-culture experiments from multiple BMEC, NPC and astrocyte isolations. Percent increases denoted in the text refer to TEER increases relative to the control at the time points of interest (24 or 48 hours). The initial increase in TEER for the control BMEC cultures observed at 24 hours was reproducible, and was a result of the reduction in serum content upon the switch to mitogen-free medium.

Comparison of Barrier Induction Mediated by Postnatal Astrocytes Versus Embryonic NPC Although the majority of the NPC-derived cells in the BMEC-NPC co-cultures were nestin positive, small percentages of astrocytes (GFAP) or immature astrocytes (GFAP/nestin) were present. Thus, in an effort to distinguish between the effects commonly associated with astrocytes and those mediated by dividing and differentiating NPC, the TEER induction properties of these two situations were directly compared. In parallel to NPC-BMEC co-culture, BMEC were also co-cultured with postnatal (P6) astrocytes at a density corresponding to the number of GFAP-positive cells (25%) counted in the BMEC-NPC co-culture experiment. Based on these counts, BMEC were co-cultured either with astrocytes (6.25×10$^4$/cm$^2$) or NPC (2.5×10$^5$/cm$^2$), and the TEER was monitored as a function of time (FIG. 7). The data indicate that NPC induced a 24% increase in BMEC TEER (96±5 Ω×cm$^2$) compared with the untreated control after just 24 hours (77±5 Ω×cm$^2$), while astrocytes did not induce a statistically significant increase in TEER (78±4 Ω×cm$^2$) during that time period. The maximum TEER reached by the astrocyte co-culture was similar to that achieved by NPC and was detected after 48 hours in co-culture where astrocytes (97±5 Ω×cm$^2$) result in a 38% increase in TEER. By 72 hours, the TEER in NPC co-culture decreased to the level of the monoculture control. However, in the case of astrocyte co-culture, the TEER remained elevated out to 120 hours. To investigate whether the lower overall density of astrocytes compared with NPC contributed to the delay in inductive response, co-culture of BMEC was also performed with a confluent monolayer of astrocytes. The higher density astrocyte co-culture yielded the same magnitude of TEER induction and the same temporal response as that seen for the low-density astrocyte co-culture, including the delay in TEER induction (data not shown).

Discussion

In this study, the influences of NPC on the BBB properties of BMEC were investigated. An in vitro model consisting of primary rat BMEC and embryonic NPC was evaluated for its barrier properties and compared with a BMEC model lacking NPC. NPC significantly influenced BMECs by inducing TEER, reducing permeability, and affecting tight junction structure. Barrier-inducing effects were only observed in the presence of differentiating NPC, while proliferating NPC in the presence of mitogens yielded no influence on BMEC monolayer TEER. Finally, barrier-strengthening effects elicited by NPC were distinguishable from astrocytic induction in terms of both the timing and duration of TEER induction. To our knowledge, this is the first demonstration of the direct influence of NPC on BBB properties of BMEC.

The increase in BMEC TEER was detectable after 24 hours of co-culture with NPC in mitogen-free medium and correlated with a decrease in fluorescein permeability. Since fluorescein is a small molecule that does not appreciably cross the BBB in vivo (Hoffman and Olszewski 1961), these measurements serve as a barometer for the functional impermeability of BBB models. The absolute TEER values (70-120 Ω×cm$^2$) achieved in this study were typical of TEER values reported for other rat and mouse BBB models (de Vries et al. 1996; Perriere et al. 2005; Weidenfeller et al. 2005; Calabria et al. 2006; K is et al. 2001). Also, as a comparison, the effect of NPC on the BMEC fluorescein permeability (3.3±0.5×10$^4$ cm/min, 33% permeability reduction) was of a similar magnitude to that previously observed upon co-culturing rat BMEC with astrocytes (2.7×10$^{-4}$ cm/min, (K is et al. 2001;

Perriere et al. 2005)). It was possible that the observed effects resulted from a higher BMEC density on the filter membrane. However, NPC did not influence the endothelial cell density and did not yield higher numbers of proliferating BMEC. Therefore, it was concluded that NPC induction of BMEC properties was not simply based on a more tightly packed monolayer, nor was it a result of newly formed BMEC having optimized properties because they were generated in the presence of NPC influences. Instead, the effect correlated with tight junction fidelity as a large fraction of the BMEC possess junctions that are continuous in the presence of NPC (33.5% frayed, 110 $\Omega \times cm^2$), while in the absence of NPC cell-cell junctions are predominantly frayed (65.1% frayed, 75 $\Omega \times cm^2$). The decrease in frayed BMEC tight junctions has also been previously noted to correlate with higher TEER and lower permeability in BMEC cultures (Weidenfeller et al. 2005; Calabria et al. 2006). Similar to the case with NPC induction, treatment with BBB-inducing glucocorticoids such as corticosterone (21% frayed, 168 $\Omega \times cm^2$) or hydrocortisone (12% frayed, 218 $\Omega \times cm^2$) decreases the number of frayed junctions and increases the TEER while also lowering the fluorescein permeability ($0.66 \times 10^4$ cm/min for hydrocortisone) (Weidenfeller et al. 2005; Calabria et al. 2006). Taken together, these results suggest that the improved barrier properties in the presence of NPC are likely a result of improved cell-cell junctional contacts.

Since the BMEC and NPC were separated by a microporous filter membrane and 1 mm of culture medium (FIG. 1), the barrier induction was clearly mediated by soluble factors. The induction was observed in mitogen-free medium as NPC begin differentiating into astrocytes and neurons, but it was not detectable in the presence of mitogens that keep NPC in an undifferentiated, nestin-positive state (Gage 2000; Ostenfeld et al. 2002). This finding suggests that some component of the differentiation process is likely required for BMEC barrier induction and that NPC proliferating in an undifferentiated state do not have a major influence. Although the presence of mitogens themselves might have influenced the integrity of the BMEC monolayer thereby masking the effects of factors released by proliferating, nestin-positive NPC (Sobue et al. 1999), this was not evident from TEER measurements of control BMEC in mitogen-containing medium. The lack of BMEC induction in the presence of 3T3 fibroblasts, proliferating nestin-positive NPC or postnatal astrocytes at 24 hours also indicates that the observed induction with differentiating NPC is not a generic trophic response due to the presence of another proliferating cell type, but instead shows that the properties specific to differentiating NPC are required. When BMEC were cultured in medium that was conditioned by differentiating NPC for 24 h, no TEER induction was detected. Therefore, the BMEC presence during the NPC differentiation process was required for the NPC to release BBB-inducing soluble factors, and this finding implicates a bidirectional communication between BMEC and NPC. The requisite interaction between NPC and BMEC was further validated by demonstrating the capacity of co-culture conditioned medium to increase the TEER when serially applied to fresh BMEC monolayers. In order to determine if pre-differentiated NPC lacking early BMEC influences release inductive factors, NPC were pre-differentiated in the absence of mitogens and subsequently added to the BMEC monolayer. After 24 h in co-culture, only a slight increase in BMEC TEER was detectable (11% pre-differentiated versus 47% co-differentiating NPC). Subsequent to 24 hours of pre-differentiation in the absence of BMEC, less than 50% of the NPC are undifferentiated (nestin-positive only), likely weakening the effect that differentiating cells can have compared with a situation where co-culture is started with a highly pure population of undifferentiated NPC. These observations support the conclusion that differentiating NPC, rather than differentiated (tubulin- or GFAP-positive) or proliferating (nestin-positive) NPC, stimulate BMEC barrier induction.

NPC proliferate as nestin-positive cells and differentiate into neurons, astrocytes, and oligodendrocytes in mitogen-free conditions (Ostenfeld et al. 2002; Ostenfeld and Svendsen 2004). Thus, NPC-derived astrocytes or neurons could be responsible for the TEER induction. Numerous studies have demonstrated that astrocytes and neurons have the potential to modulate BBB tight junctions, transporter expression, and metabolic activity in vitro and in vivo (Stewart and Wiley 1981; Risau et al. 1986b; Savettieri et al. 2000). Very few βIII tubulin-positive neurons and βIII tubulin/nestin co-positive cells (10% combined) were generated in the presence of BMEC. Also since more neurons are present when NPC are pre-differentiated prior to co-culture but the resulting inductive effect lessened, βIII tubulin-positive neurons do not appear to play a significant role in the observed induction process. Nearly 16% of the NPC-derived cells were positive for both GFAP and nestin, indicating that the second largest population of cells is committed to the astroglial fate but has not yet fully matured. Only 10% were mature astrocytes as defined by GFAP expression. Although astrocytes are strong inducers of BBB properties, the timecourse of TEER induction by NPC indicated that NPC acted earlier while astrocyte effects were more prolonged. Similarly, the pre-differentiated NPC cultures having 25% GFAP-positive cells also exhibited only weak inductive properties after 24 hours (FIG. 2, column 3). Interestingly, the NPC and astrocytes caused the BMEC to reach a similar maximum TEER value indicating a comparable absolute induction capacity of NPC and astrocytes under these experimental conditions, although the dynamics of induction clearly differed. While this study cannot entirely exclude the possibility that NPC-derived astrocytes are providing the inductive signals, these data strongly suggest that differentiating NPC and astrocytes function via distinct induction mechanisms or at the very least, different temporal programs.

In addition to the inductive signals provided by NPC, BMEC also influenced the morphology and differentiation of NPC, further implicating a bidirectional paracrine interaction. The findings of a flattened precursor-like progeny and decreased neuronal production in the presence of primary BMEC corroborate the results of a previous study that employed brain endothelial cell lines or pulmonary artery endothelial cells in embryonic neural stem cell co-cultures (Shen et al. 2004). In addition, this previous study also demonstrated that upon removal of the endothelial cells, neurogenesis was increased (Shen et al. 2004). Other investigations have also implicated endothelial involvement in NPC regulation by showing that endothelial cells assist in the recruitment of newly formed neurons (Louissaint et al. 2002) and stimulate astrocyte precursor differentiation into GFAP- and S100β-expressing mature astrocytes (Mi et al. 2001). It also has been suggested that progenitor contact with microvessels during development favors the astrocyte lineage (Zerlin and Goldman 1997). Finally, NPC are also found in various regions of the adult brain in close proximity to the vasculature in the so-called stem cell niche (Doetsch 2003b), In the adult, neurogenesis occurs in foci closely associated with blood vessels (Palmer et al. 2000). There is also evidence implying that angiogenesis and neurogenesis may be co-regulated since they are stimulated by many of the same factors, such as bFGF, VEGF, IGF-1 and TGFβ. In addition, endothelial cells secrete known neuronal differentiation and survival factors (bFGF, IGF-1, VEGF, PDGF, IL8 and BDNF) and a link between angiogenesis and neurogenesis is found in the adult songbird brain during testosterone-induced angiogenesis (Palmer et al. 2000; Jin et al. 2002; Louissaint et al. 2002). Thus, bidirectional BMEC-NPC communication could play important roles in both embryonic development and adult brain plasticity.

The predominant cell types in the developing brain cortex at day E14 are NPC, radial glia, neuroblasts, and neurons (FIG. 6, and references (Bass et al. 1992; Saunders et al. 2000; McCarty et al. 2002; Doetsch 2003a)). These cells are found in close proximity to and in contact with developing brain vessels in vivo. The appearance of BBB endothelial properties in vivo occurs shortly after the blood vessels invade the embryonic brain as endothelial cells begin to thin (Bauer et al. 1993; Stewart and Hayakawa 1994; Bolz et al. 1996), brain vessel permeability decreases and the TEER increases (Risau et al. 1986a; Bauer et al. 1995). These early stages of BBB development take place while astrocytes are scarce in the developing brain (FIG. 6, and reference (LeVine and Goldman 1988)). Therefore, it is entirely plausible that brain cells other than astrocytes may be able to induce early BBB properties in brain endothelial cells. In the developing brain environment, the NPC differentiation process could provide the cues necessary for naïve brain EC to acquire initial BBB properties; whereas, in later stages of development, astrocytes would induce further maturation and help maintain BBB properties in differentiated EC (FIG. 7). Accordingly, the observations provided in this study indicate that differentiating NPC may be important for such early onset of BBB properties in the developing embryonic brain, although additional study will be necessary to define the exact physiological impact of the reported BMEC-NPC interactions. Despite the fact that the yields of naïve embryonic brain endothelial cells would be prohibitively low for the study described here, it is intriguing to consider using an in vitro model that employs embryonic BMEC or even stem cell-derived EC to provide additional insight into the process of BBB and NPC co-development.

Example II

Co-Culture of BMEC with Predifferentiated NPC

NPC were isolated from E14 rat brains and expanded for 1 week in FGF2 and EGF containing medium as described in Example I (EGF, 20 ng/mL), fibroblast growth factor (FGF-2, 20 ng/mL), and heparin (5 µg/mL). During expansion, half of the medium was replaced with fresh mitogen-containing medium every 3 days. After one week, NPC were cryo-preserved as single cells digested with ACCUTASE™ enzyme mixture. After thawing, NPC were allowed to recover for 4 days in nitrogen-containing medium, and after formation of spheres, cells were digested with Accutase™ and live cells were counted on a hemacytometer. $2.5 \times 10^5$ NPC/cm$^2$ were plated in the lower compartment in mitogen-free medium allowing NPC differentiation [DMEM:HAMS-F12 at 3:1, 2% v/v B27, Invitrogen Corp. (Carlsbad, Calif.)], and antibiotic-antimycotic solution (100 U/mL penicillin, 100 mg/mL streptomycin, and 0.25 mg/mL amphotericin), with poly L-lysine/laminin coating. The differentiation medium was exchanged every 3 days and after 6-14 days in culture, the TRANSWELL™ filter containing the confluent BMEC was then added to complete the co-culture system.

Figure 8:
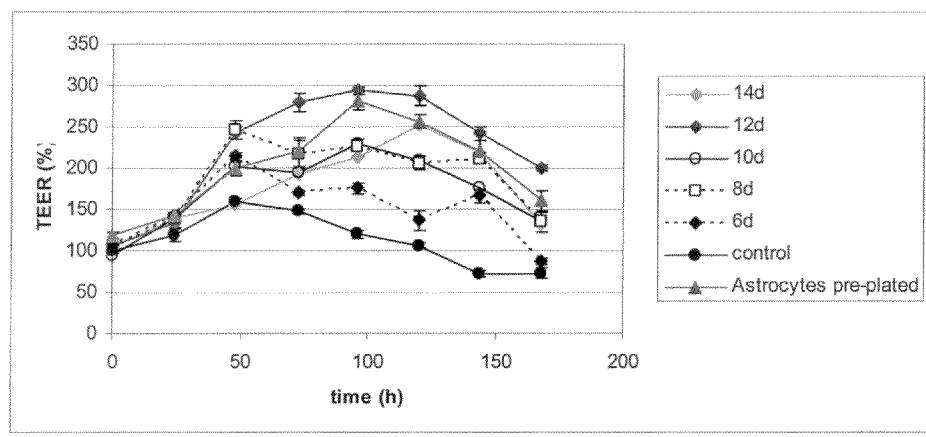
FIG. 8: TEER measurements of BMEC in co-culture with NPC-derived astrocyte and neuron mixed cultures or postnatal primary astrocytes. Postnatal primary astrocytes, or predifferentiated NPC (differentiation process induced 6, 8, 10, 12, and 14 days prior starting the co-culture) were co-cultured with confluent BMEC using mitogen-free culture medium, and the TEER timecourse was followed for 7 days. Predifferentiated NPC were prepared as follows: NPC were expanded after isolation for one week. Spheres were digested with ACCUTASE™ enzyme mixture, frozen down, and stored in liquid nitrogen until further use. 4 days prior induction of differentiation, NPC were thawed and plated in NPC culture media to form spheres. The differentiation of spheres digested with ACCUTASE™ enzyme mixture was induced by mitogen removal from the culture medium and plating on poly L-lysine/laminin coated 12 well plates ($2 \times 10^5$ cells/cm$^5$). The medium was changed every three days. At 6, 8, 10, or 12 days after initiation of differentiation in mitogen-free medium with 1% serum the filter with confluent BMEC was added. Triplicate cultures were analyzed for each condition and the resistance measurements normalized to those of the untreated control at time zero, and results display mean±SD.

Referring to FIG. 8, NPC that were allowed to differentiate for various times prior to co-culture setup showed different inductive properties in BMEC. 12d-pre-differentiated NPC-derived mixtures from astrocytes and neurons showed the best induction in terms of TEER and performed better that postnatal primary astrocyte cultures. Pretreatment of NPC-derived astrocytes and neurons with cAMP had no influence on the magnitude of the TEER induction in BMEC.

Example III

Co-Culture of BMEC with Human Co-Differentiating NPC

Human NPC were generally cultured like rat NPC in mitogen-containing medium. Cells were initially seeded in defined serum-free NPC culture medium [DMEM:HAMS-F12 at 3:1 supplemented with B27 (2% v/v), epidermal growth factor (EGF, 20 ng/mL), fibroblast growth factor (FGF-2, 20 ng/mL), and heparin (5 µg/mL)]. During expansion, half of the medium was replaced with fresh FGF2 and EGF containing medium every 3 days and spheres were chopped every week. Before inducing the co-differentiation process, human NPC were digested with ACCUTASE™ enzyme mixture and live cells were counted on a hemacytometer, and $2.5 \times 10^5$ NPC/cm$^2$ were plated in the lower compartment in mitogen-free medium allowing the onset of NPC differentiation [DMEM:HAMS-F12 at 3:1, 1% FBS, 2% v/v B27, Invitrogen Corp. and antibiotic-antimycotic solution (100 U/mL penicillin, 100 mg/mL streptomycin, and 0.25 mg/mL amphotericin), with poly L-lysine/laminin coating]. Immediately after plating the NPC in mitogen-free medium, the TRANSWELL™ filter containing the confluent BMEC was then added to complete the co-culture system.

Figure 9:
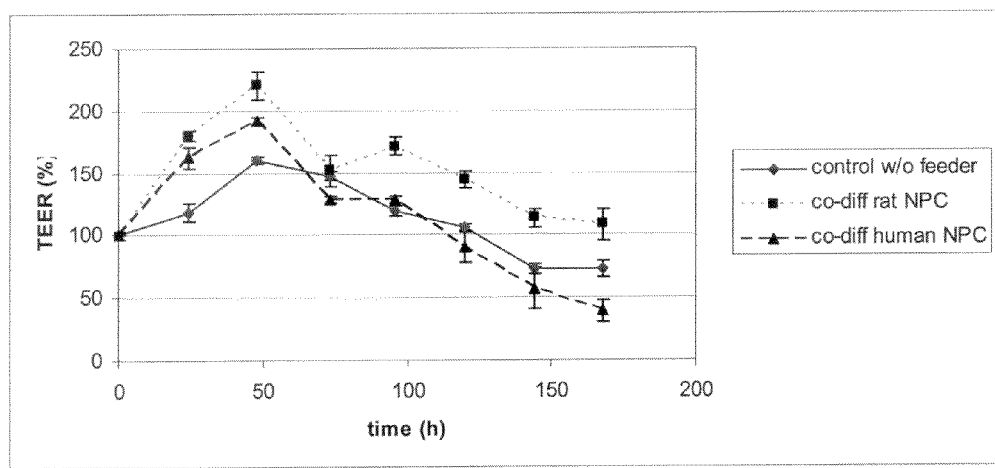
FIG. 9: TEER measurements of BMEC in co-culture with co-differentiating human and rat NPC. Co-differentiating rat and human NPC were co-cultured with confluent BMEC using mitogen-free culture medium, and the TEER timecourse was followed for 7 days. Human NPC were kept in culture for 20 weeks. Spheres were chopped once a week and re-plated in 50% fresh and 50% conditioned medium. Prior to plating the human NPC, spheres were digested with ACCUTASE™ enzyme mixture and single cells were plated in accordance with the rat NPC. Triplicate cultures were analyzed for each condition and the resistance measurements normalized to those of the untreated control at time zero, and results display mean±SD.

Referring to FIG. 9, human co-differentiating NPC showed a similar time course of TEER induction in BMEC as rat co-differentiating NPC. However the peak of induction is slightly lower in the chimeric system than in the rat system.

REFERENCES

Balabanov R. and Dore-Duffy P. (1998) Role of the CNS microvascular pericyte in the blood-brain barrier. *J Neurosci Res* 53, 637-644.

Bass T., Singer G., Slusser J. and Liuzzi F. J. (1992) Radial glial interaction with cerebral germinal matrix capillaries in the fetal baboon. *Exp Neurol* 118, 126-132.

Bauer H., Sonnleitner U., Lametschwandtner A., Steiner M., Adam H. and Bauer H. C. (1995) Ontogenic expression of the erythroid-type glucose transporter (Glut 1) in the telencephalon of the mouse: correlation to the tightening of the blood-brain barrier. *Brain Res Dev Brain Res* 86, 317-325.

Bauer H. C. and Bauer H. (2000) Neural induction of the blood-brain barrier: still an enigma. *Cell Mol Neurobiol* 20, 13-28.

Bauer H. C., Bauer H., Lametschwandtner A., Amberger A., Ruiz P. and Steiner M. (1993) Neovascularization and the appearance of morphological characteristics of the blood-brain barrier in the embryonic mouse central nervous system. *Brain Res Dev Brain Res* 75, 269-278.

Bolz S., Farrell C. L., Dietz K. and Wolburg H. (1996) Subcellular distribution of glucose transporter (GLUT-1) during development of the blood-brain barrier in rats. *Cell Tissue Res* 284, 355-365.

Butt A. M., Jones H. C. and Abbott N. J. (1990) Electrical resistance across the blood-brain barrier in anaesthetized rats: a developmental study. *J Physiol* 429, 47-62.

Calabria A. R., Weidenfeller C., Jones A. R., de Vries H. E. and Shusta E. V. (2006) Puromycin-purified rat brain microvascular endothelial cell cultures exhibit improved barrier properties in response to glucocorticoid induction. *J Neurochem* 97, 922-933.

Caley D. W. and Maxwell D. S. (1970) Development of the blood vessels and extracellular spaces during postnatal maturation of rat cerebral cortex. *J Comp Neurol* 138, 31-47.

de Vries H. E., Blom-Roosemalen M. C., van Oosten M., de Boer A. G., van Berkel T. J., Breimer D. D. and Kuiper J. (1996) The influence of cytokines on the integrity of the blood-brain barrier in vitro. *J Neuroimmunol* 64, 37-43.

Deli, M A, Abrahám, C S, Kataoka, Y, and Niwa, M. (2005) Permeability studies on in vitro blood-brain barrier models: physiology, pathology, and pharmacology *Cell Mol Neurobiol*. (1):59-127.

Doetsch F. (2003a) The glial identity of neural stem cells. *Nat Neurosci* 6, 1127-1134.

Doetsch F. (2003b) A niche for adult neural stem cells. *Curr Opin Genet Dev* 13, 543-550.

Dziegielewska K. M., Daikuhara Y., Ohnishi T., Waite M. P., Ek J., Habgood M. D., Lane M. A., Potter A. and Saunders N. R. (2000) Fetuin in the developing neocortex of the rat: distribution and origin. *J Comp Neurol* 423, 373-388.

Engelhardt B. (2003) Development of the blood-brain barrier. *Cell Tissue Res* 314, 119-129.

Enkvist M. O., Hamalainen H., Jansson C. C., Kukkonen J. P., Hautala R., Courtney M. J. and Akerman K. E. (1996) Coupling of astroglial alpha 2-adrenoreceptors to second messenger pathways. *J Neurochem* 66, 2394-2401.

Ferguson R. K. and Woodbury D. M. (1969) Penetration of 14C-inulin and 14C-sucrose into brain, cerebrospinal fluid, and skeletal muscle of developing rats. *Exp Brain Res* 7, 181-194.

Gage F. H. (2000) Mammalian neural stem cells. *Science* 287, 1433-1438.

Gallo et al. (2002) *J Cell Biology* 158, 731-40.

Gerhart D. Z., Enerson B. E., Zhdankina O. Y., Leino R. L. and Drewes L. R. (1997) Expression of monocarboxylate transporter MCT1 by brain endothelium and glia in adult and suckling rats. *Am J Physiol* 273, E207-213.

Hoffman H. J. and Olszewski J. (1961) Spread of sodium fluorescein in normal brain tissue. A study of the mechanism of the blood-brain barrier. *Neurology* 11, 1081-1085.

Janzer R. C. and Raff M. C. (1987) Astrocytes induce blood-brain barrier properties in endothelial cells. *Nature* 325, 253-257.

Jin K., Zhu Y., Sun Y., Mao X. O., Xie L. and Greenberg D. A. (2002) Vascular endothelial growth factor (VEGF) stimulates neurogenesis in vitro and in vivo. *Proc Natl Acad Sci USA* 99, 11946-11950.

Johanson C. E. (1989) Ontogeny and phylogeny of the blood-brain barrier, in *Implications of the blood-brain barrier and its manipulation* (Neuwelt E. A., ed.). Plenum, New York.

Katoh (2002) *Int. J. Mol. Med* 10, 683-687.

Kaufman et al., U.S. Pat. No. 7,176,023

K is B., Deli M. A., Kobayashi H., Abraham C. S., Yanagita T., Kaiya H., Isse T., Nishi R., Gotoh S., Kangawa K., Wada A., Greenwood J., Niwa M., Yamashita H. and Ueta Y. (2001) Adrenomedullin regulates blood-brain barrier functions in vitro. *Neuroreport* 12, 4139-4142.

Kniesel U., Risau W. and Wolburg H. (1996) Development of blood-brain barrier tight junctions in the rat cortex. *Brain Res Dev Brain Res* 96, 229-240.

Krizbai I. A. and Deli M. A. (2003) Signalling pathways regulating the tight junction permeability in the blood-brain barrier. *Cell Mol Biol (Noisy-le-grand)* 49, 23-31.

Kubo et al. (2005) *Blood*, 105, 4590-4597.

LeVine S. M. and Goldman J. E. (1988) Embryonic divergence of oligodendrocyte and astrocyte lineages in developing rat cerebrum. *J Neurosci* 8, 3992-4006.

Louissaint A., Jr., Rao S., Leventhal C. and Goldman S. A. (2002) Coordinated interaction of neurogenesis and angiogenesis in the adult songbird brain. *Neuron* 34, 945-960.

McCarty J. H., Monahan-Earley R. A., Brown L. F., Keller M., Gerhardt H., Rubin K., Shani M., Dvorak H. F., Wolburg H., Bader B. L., Dvorak A. M. and Hynes R. O. (2002) Defective associations between blood vessels and brain parenchyma lead to cerebral hemorrhage in mice lacking alphav integrins. *Mol Cell Biol* 22, 7667-7677.

Mi H., Haeberle H. and Barres B. A. (2001) Induction of astrocyte differentiation by endothelial cells. *J Neurosci* 21, 1538-1547.

Nico B., Quondamatteo F., Herken R., Marzullo A., Corsi P., Bertossi M., Russo G., Ribatti D. and Roncali L. (1999) Developmental expression of ZO-1 antigen in the mouse blood-brain barrier. *Brain Res Dev Brain Res* 114, 161-169.

Ostenfeld and Svendsen (2003) *Adv Tech Stand Neurosurg*, 28:3-89

Ostenfeld T. and Svendsen C. N. (2004) Requirement for neurogenesis to proceed through the division of neuronal progenitors following differentiation of epidermal growth factor and fibroblast growth factor-2-responsive human neural stem cells. *Stem Cells* 22, 798-811.

Ostenfeld T., Joly E., Tai Y. T., Peters A., Caldwell M., Jauniaux E. and Svendsen C. N. (2002) Regional specification of rodent and human neurospheres. *Brain Res Dev Brain Res* 134, 43-55.

Palmer T. D., Willhoite A. R. and Gage F. H. (2000) Vascular niche for adult hippocampal neurogenesis. *J Comp Neurol* 425, 479-494.

Perriere N., Demeuse P., Garcia E., Regina A., Debray M., Andreux J. P., Couvreur P., Scherrmann J. M., Temsamani J., Couraud P. O., Deli M. A. and Roux F. (2005) Puromycin-based purification of rat brain capillary endothelial cell cultures. Effect on the expression of blood-brain barrier-specific properties. *J Neurochem* 93, 279-289.

Ramsauer M., Krause D. and Dermietzel R. (2002) Angiogenesis of the blood-brain barrier in vitro and the function of cerebral pericytes. *Faseb J* 16, 1274-1276.

Risau W., Hallmann R. and Albrecht U. (1986a) Differentiation-dependent expression of proteins in brain endothelium during development of the blood-brain barrier. *Dev Biol* 117, 537-545.

Risau W., Hallmann R., Albrecht U. and Henke-Fahle S. (1986b) Brain induces the expression of an early cell surface marker for blood-brain barrier-specific endothelium. *Embo J* 5, 3179-3183.

Saunders N. R., Knott G. W. and Dziegielewska K. M. (2000) Barriers in the immature brain. *Cell Mol Neurobiol* 20, 29-40.

Savettieri G., Di Liegro I., Catania C., Licata L., Pitarresi G. L., D'Agostino S., Schiera G., De Caro V., Giandalia G., Giannola L. I. and Cestelli A. (2000) Neurons and ECM regulate occludin localization in brain endothelial cells. *Neuroreport* 11, 1081-1084.

Schulze C. and Firth J. A. (1992) Interendothelial junctions during blood-brain barrier development in the rat: morphological changes at the level of individual tight junctional contacts. *Brain Res Dev Brain Res* 69, 85-95.

Segovia J., Lawless G. M., Tillakaratne N. J., Brenner M. and Tobin A. J. (1994) Cyclic AMP decreases the expression of a neuronal marker (GAD67) and increases the expression of an astroglial marker (GFAP) in C6 cells. *J Neurochem* 63, 1218-1225.

Shen Q., Goderie S. K., Jin L., Karanth N., Sun Y., Abramova N., Vincent P., Pumiglia K. and Temple S. (2004) Endothelial cells stimulate self-renewal and expand neurogenesis of neural stem cells. *Science* 304, 1338-1340.

Sobue K., Yamamoto N., Yoneda K., Hodgson M. E., Yamashiro K., Tsuruoka N., Tsuda T., Katsuya H., Miura Y., Asai K. and Kato T. (1999) Induction of blood-brain barrier properties in immortalized bovine brain endothelial cells by astrocytic factors. *Neurosci Res* 35, 155-164.

Stewart P. A. and Wiley M. J. (1981) Developing nervous tissue induces formation of blood-brain barrier characteristics in invading endothelial cells: a study using quail-chick transplantation chimeras. *Dev Biol* 84, 183-192.

Stewart P. A. and Hayakawa K. (1994) Early ultrastructural changes in blood-brain barrier vessels of the rat embryo. *Brain Res Dev Brain Res* 78, 25-34.

Tontsch U. and Bauer H. C. (1991) Glial cells and neurons induce blood-brain barrier related enzymes in cultured cerebral endothelial cells. *Brain Res* 539, 247-253.

Weidenfeller C., Schrot S., Zozulya A. and Galla H. J. (2005) Murine brain capillary endothelial cells exhibit improved barrier properties under the influence of hydrocortisone. *Brain Res* 1053, 162-174.

Weidenfeller, C., Svendsen, C., and Shusta, E. (2007) Differentiating embryonic neural progenitor cells induce blood-brain barrier properties *Journal of Neurochemistry* 101 (2), 555-565. (Incorporated by reference)

Wurmser A. E., Nakashima K., Summers R. G., Toni N., D'Amour K. A., Lie D. C. and Gage F. H. (2004) Cell fusion-independent differentiation of neural stem cells to the endothelial lineage. *Nature* 430, 350-356.

Zerlin M. and Goldman J. E. (1997) Interactions between glial progenitors and blood vessels during early postnatal corticogenesis: blood vessel contact represents an early stage of astrocyte differentiation. *J Comp Neurol* 387, 537-546.

We claim:

1. A method of analyzing the blood-brain barrier permeability characteristics of a model compound comprising the steps of:
a) creating a multicellular blood-brain barrier model by culturing brain microvascular endothelial cells upon a permeable support in the presence of pre-differentiated multipotent neural progenitor cells wherein the endothelial cells form a monolayer wherein the cells are confluent and express and initial transendothelial electrical resistance (TEER) of 20-50 Ohm×cm$^2$ before exposure to the neural cells, and wherein the pre-differentiated multipotent neural progenitor cells further differentiate into mixtures of astrocytes, neurons and oligodendrocytes, wherein the TEER is greater than 100 Ohm×cm$^2$ after exposure to the differentiated neural cells and wherein the model is then capable of a TEER of greater than 100 Ohm×cm$^2$ for a period of at least 72 hours;
b) exposing a model compound to the blood-brain barrier model resulting from step (a), and
c) measuring the permeability of the barrier model to the compound.

2. The method of claim 1 wherein the measurement is by determination of compound concentration in on each side of the brain microvascular endothelial cell monolayer.

3. The method of claim 1 wherein the endothelial cells are isolated from mammalian brain capillaries in step (a).

4. The method of claim 1 wherein the endothelial cells are derived from isolated embryonic stem cells in step (a).

5. The method of claim 1 wherein the TEER is greater than 200 Ohm×cm$^2$ after exposure to the neural cells in step (a).

6. The method of claim 1 wherein the neural progenitor cells are isolated from mammalian cortices in step (a).

7. The method of claim 6 wherein the neural cells are digested with at least one enzyme to dissociate the cells.

8. The method of claim 1 wherein the neural progenitor cells are grown as free-floating neurospheres before differentiation in step (a).

9. The method of claim 1 wherein the neural cells are removed after the endothelial cells are confluent and wherein the endothelial cells express a TEER of at least 100 Ohm×cm$^2$.

* * * * *

UNITED STATES PATENT AND TRADEMARK OFFICE
CERTIFICATE OF CORRECTION

| | |
|---|---|
| PATENT NO. | : 8,293,495 B2 |
| APPLICATION NO. | : 13/218123 |
| DATED | : October 23, 2012 |
| INVENTOR(S) | : Eric V. Shusta et al. |

It is certified that error appears in the above-identified patent and that said Letters Patent is hereby corrected as shown below:

Column 24, Claim 1, line 10, "express and initial" should be -- express an initial --

Column 24, Claim 2, line 24, "concentration in on" should be -- concentration on --

Signed and Sealed this
Eleventh Day of December, 2012

David J. Kappos
*Director of the United States Patent and Trademark Office*